US007879866B2

(12) United States Patent
Gram et al.

(10) Patent No.: US 7,879,866 B2
(45) Date of Patent: Feb. 1, 2011

(54) INHIBITION OF THE ACTIVITY OF THE CAPSAICIN RECEPTOR IN THE TREATMENT OF OBESITY OR OBESITY-RELATED DISEASES AND DISORDERS

(75) Inventors: Dorte Xenia Gram, Copenhagen Ø (DK); Anker Jon Hansen, Charlottenlund (DK)

(73) Assignee: Dorte Xenia Gram, Copenhagen Ø (DK)

( * ) Notice: Subject to any disclaimer, the term of this patent is extended or adjusted under 35 U.S.C. 154(b) by 491 days.

(21) Appl. No.: 11/632,818

(22) PCT Filed: Jul. 18, 2005

(86) PCT No.: PCT/DK2005/000502

§ 371 (c)(1),
(2), (4) Date: Sep. 17, 2007

(87) PCT Pub. No.: WO2006/007851

PCT Pub. Date: Jan. 26, 2006

(65) Prior Publication Data

US 2008/0214574 A1 Sep. 4, 2008

Related U.S. Application Data

(60) Provisional application No. 60/589,242, filed on Jul. 20, 2004.

(30) Foreign Application Priority Data

Jul. 19, 2004 (DK) ................................ 2004 01126

(51) Int. Cl.
 *A61K 31/519* (2006.01)
 *A61K 31/517* (2006.01)
 *A61K 31/335* (2006.01)
(52) U.S. Cl. ............................ 514/264.11; 514/266.2; 514/449; 514/909
(58) Field of Classification Search ............ 514/264.11, 514/266.2, 449, 909
See application file for complete search history.

(56) References Cited

U.S. PATENT DOCUMENTS

| 4,598,089 A * | 7/1986 | Hadvary et al. ............. 514/449 |
| 7,074,799 B2 * | 7/2006 | Bakthavatchalam et al. ...... 514/264.11 |

FOREIGN PATENT DOCUMENTS

| WO | WO 00/42023 | 7/2000 |
| WO | WO 02/08211 | 1/2002 |
| WO | WO 02/072536 | 9/2002 |
| WO | WO 02/76946 | 10/2002 |
| WO | WO 02/090326 | 11/2002 |
| WO | WO 03/014064 | 2/2003 |
| WO | WO 03/022809 | 4/2003 |
| WO | WO 03/062209 | 7/2003 |
| WO | WO 03/066595 | 8/2003 |
| WO | WO 2004/055003 | 7/2004 |
| WO | WO 2004/056774 | 7/2004 |

OTHER PUBLICATIONS

PCT Search Report dated Jul. 26, 2006 for PCT/DK2005/00502.
Gray. A. et al., Cost Effectiveness of an Intensive Blood Glucose Control Policy in Patients With Type 2 Diabetes: Economic Analysis Alongside Randomised Controlled Trial (UKPDS 41)., United Kingdom Prospective Diabetes Study Group, FMJ 320, 1373-1378 2000.
U.K. Prospective Diabetes Study Group. UKPDS 40. Cost Effectiveness Analysis of Improved Blood Pressure Control in Hypertensive Patients with Type 2 Diabetes. BMJ 317, 720-726 (1998).
Mann, J., Stemming the Tide of Diabetes Mellitus., Lancet 356, 1454-1455, 2000.
Knowler, W.C. et al., Reduction in the Incidence of Type 2 Diabetes with Lifestyle Intervention or Metformin, New Engl. J. Med., 346, 393-403, 2002.
Fagerberg., B., Bokemark, L. & Hulthe, J., The Metabolic Syndrome, Smoking, and Antibodies to Oxidized LDL in 58-year-old Clinically Healthy Men., Nutr. Metab. Carbiovasc. Disc., 11, 227-235, 2001.
Liu, S. et al., Relation Between a Diet with a High Glycemic Load and Plasma Concentrations of High-Sensitivity C-reactive Protein in Middle-aged Women,<sup>1-3</sup>. Am. J. Clin. N. 75, 492-498, 2002.
Temelkova-Kurktschiev, T., Subclinical Inflammation in Newly Detected type II Diabetes and Impaired Glucose Tolerance, 3, Diabetolog 45, 151-2002.
Festa, A., et al, Chronic Subclinical Inflammation as Part of the Insulin Resistance Syndrome—The Insulin Resistance Atherosclerosis Study (IRAS), Circulation 102, 42-47, 2000.
Bhally, H.S. & Livtin, Y., Association Between HbA1C and Serum C-Reactive Protein Levels in Diabetes Mellitus, Diabetes 50, A90, 2001.
Weyer, C., et al., Humoral Makers of Inflammation and Endothelial Dysfunction in Relation to Adiposity and in Vivo Insulin Action in Pima Indians, Atherosclerosis 161, 233-242, 2002.
Julius, D. & Basbaum, A.I., Molecular Mechanisms of Nociception, Nature 413, 203-210, 2001.
Szolcsanyi, J., Jancso-Gabor, A., & Joo, F., Functional and Fine Structural Characteristics of the Sensory Neuron Blocking Effect of Capsaicin, Naunyn Schmiedebergs Arch Pharmacol 287, 157-169, 1975.

(Continued)

*Primary Examiner*—Kevin Weddington
(74) *Attorney, Agent, or Firm*—Woodcock Washburn LLP (57) ABSTRACT

The present invention provides a method of treating diseases or disorders benefiting from inactivating or down regulating the activity of the capsaicin receptor in a mammal by inhibiting the activity of the capsaicin receptor.

The present invention also provides a method of treating obesity and obesity-related diseases and disorders in a mammal by inhibiting the activity of the capasaicin receptor.

5 Claims, 4 Drawing Sheets

OTHER PUBLICATIONS

Barrachina, M.D., Martinez, V., Wei, J.Y. & Tache, Y., Leptin and CCK Interact to Reduce Food Intake in Lean Mice: Role of Capsaicin-Sensitive Afferent Neurons, Methods and Findings in Experimental and Clinical Pharmacology 19, 85, 1997.

Jancso-Gabor, A., Szoldsanyi, J. & Jancso, N., Irreversible Impairment of Thermo Regulation Induced by Capsaicin and Similar Pungent Substances in Rats and Guinea Pigs., J Physiol, London 206, 495-507, 1970.

Blumberg, P.M., Szallasi, A., & Acs, G., Resiniferatoxin: An Ultrapotent Capsaicin Analogue, Br. J. Pharmacol, 110, 45-62, 1993.

Szallasi, A. & Blumberg, P.M., Resiniferatoxin, a Phorbol-Related Diterpene, Acts as an Ultrapotent Analog of Casaicin, the Irritant Constituent in Red Pepper, Neuroscienc 30, 4515-520, 1989.

Davey, P.T., Banner, S.E., Hamilton, T.C. & Sanger, G.J., Inhibition by Capsazepine and Ruthenium Red of the Pro- and Anti-Nociceptive Effects of Olvanil, Br. J. Pharmacol, 115, 100P-1995.

Wittka, R., Wieland, H., Meyes, H. & Denzer, D., Comparison of Two Vanilloid Receptor Agonists: Capsaicin and Olvanil, Life Sci, 26, Abstract-391, 2000.

Ralevic, V., Kendall, D.A., Jerman, J.C., Middlemiss, D.N. & Smart, D., Cannabinoid Activation of Recombinant and Endogenous Vanilloid Receptors, Eur. J. Pharmacol, 424, 211-219, 2001.

Ahern, G.P. & Premkumar, L.S., PKC Induces Vanilloid Receptor Channel Activity, Biophysical Journal 80, 208a, 2001.

Pomonis, J.D., et al., N-(4-Tertiarybutylphenyl)-4-(3-Cholorphyridin-2-yl) Tetrahydropyrazine-1(2H)-CARBOXAMIDE (bctc), a Novel, Orally Effective Vanilloid Receptor 1 Antagonist with Analgesic Properties: II. In Vivo Characterization in Rat Models of Inflammatory and Neuropathic Pain, J. Pharmacol. Exp. Ther. 306, 387-393, 2003.

Valenzano, K.J. et al., N-(4-tertiarybutylphenyl)-4-(3-chloropyridini-2-yl)tetrahydropyrazine-1(2H)-carbox-amide (BCTC), A Novel, Orally Effective Vanilloid Receptor 1 Antagonist with Analgesic Properties: I. In Vitro Characterization and Pharmacokinetic Properties, J. Pharmacol. Exp. Ther. 306, 377-386, 2003.

Karlsson, S., Scheurink, A., Steffens, A. & Ahren, b., Increased Insulin Secretion and Glucose Tolerance After Neonatal Capsaicin in Mice, Diabetolog 37, A43, 1994.

Koopmans, S.J., Leighton, B. & Defronzo, R.A., Neonatal Deafferentation of Capsaicin-Sensitive Sensory Nerves Increases in Vivo Insulin Sensitivity in Conscious Adult Rats, Diabetolog 41, 813-820, 1998.

Gram, D.X. et al., Basal Glycaemia and Glucose Tolerance is Improved After Resiniferatoxin in Male Zucker Diabetic Fatty Rats, Diabetologia 44 (Supplement 1), A 178, 2001.

Gram, D.X. et al., Capsaicin Desensitisation Delays the Progression of Type 2 Diabetes in the Zucker Fatty Rat, Diabetes 49 (Supplement 1), A428, 2000.

Gram, D.X., Brand, C.L., Wilken, M., Riebel, U. & Carr, R.D. DDPIV Activity is Decreased and Glucose Tolerance Improved By Sensory Nerve Denervatiion in the ZDF Rat, Diabetes 50 (Suppl. 2), A515, 2167-PO, 2001.

Gram, D.X. et al., Sensory Nerve Desensitisation in Zucker Diabetic Fatty Rats Preserves in Vitro Insulin Secretion, Diabetologia 43 (Supplement 1), A130, 2000.

Moesgaard, S. et al., Sensory Nerve Inactivation by Resiniferatoxin Improves Insulin Sensitivity in Male Obese Zucker Rats, Diabetes 52, A68-2003.

Caterina, M.J. et al., The Capsaicin Receptor: A Heat-Activated Ion Channel in the Pain Pathway, Nature (Lond), 389, 816-824, 1997.

Caterina, M.J. & Julius, D., The Vanilloid Receptor: A Molecular Gateway to the Pain Pathway, Annu. Rev. Neurosci. 24, 487-517, 2001.

Mezey, E. et al., Distribution of mRNA for Vanilloid Receptor Subtype 1 (VR1), and VR1-like Immunoreactivity, in the Central Nervous System of the Rat and Human, Proc. Natl. Acad. Sci. U.S.A., 97, 3655-3660, 2000.

Cortright, D.N. & Szallasi, A., Biochemical Pharmacology of the Vanilloid Receptor TRPV1—An Update, Eur. J. Biochem 271, 1814-1819, 2004.

Smart, D. et al., The Endogeneous Lipid Anandamide is a Full Agonist at the Human Vanilloid Receptor (hVR1), Br. J. Pharmacol 129, 227-230, 2000.

Caterina, M.J. et al., Impaired Nociception and Pain Sensation in Mice Lacking the Capsaicin Receptor, Science, Wasington, DC, 288, 306-313, 2000.

Davis, J.B. et al., Vanilloid Receptor-1 is Essential for Inflammatory Thermal Hyperalgesia, Nature, 405, 183-187, 2000.

Ahren, B. & Pacini, G., Insufficient Islet Compensation to Insulin Resistance vs. Reduced Glucose Effectiveness in Glucose-Intolerant Mice, American Journal of Physiology, Endocrinology and Metabolism 283, E738-E744, 2002.

La Fleur, S.E., Kalsbeek, A., Wortel, J., Fekkes, M.L. & Buijs, R.M., A Daily Rhythm in Glucose Tolerance: A Role for the Suprachiasmatic Nucleus, Diabetes 50, 1237-1243, 2001.

Wahl, P., Foged, C., Tullin, S. & Thomsen, C., Iodoresiniferatoxin, a New Potent Vanilloid Receptor Antagonist, Mol. Pharmacol 59, 9-15, 2001.

Seabrook, G.R. et al., Functional Properties of the High-Affinity TRPV1 (VR1) Vanilloid Receptor Antagonist (4-hydroxy-t-iodo-3-methoxyphenylacetate ester) iodoresiniferatoxin, J. Pharmacol. Exp. Ther. 303, 1052-1060, 2002.

Lee, J. et al., N-(3-acyloxy-2-benzylpropyl)-N'[4-(methylsulfonylamino) benzyl] thioure a analogues: Novel Potent and High Affinity Antagonists and Partial Antagonists of the Vanilloid Receptor, J. Med. Chem 46, 3116-3126, 2003.

Wang, Y. et al., High Affinity Antagonists of the Vanilloid Receptor, Mol. Pharmacol. 62, 947-956, 2002.

Toth, A., Blumberg, P.M., Chen Z. & Kozikowski, A.P., Design of a High-Affinity Competitive Antagonist of the vanilloid Receptor Seelctive for the Calcium Entry-Linked Receptor Population, Mol. Pharmacol., 65, 282-291, 2004.

Yoon, J. et al., Chain-branched Acyclic phenethylthiocarbamates as Vanilloid Receptor Antagonists, Bioorganic & Medicinal Chemistry Letters 13, 1549-1552, 2003.

McDonnell, M.E., Zhang, S., Nasser, N. Dubin, A.E. & Dax, S.L., 7-Hydroxynaphthalen-1-yl-urea and -amide antagonists of Human Vanilloid Receptor 1., Bioorganic & Medicinal Chemistry Letters 14, 531-534, 2004.

Sun, Q. et al., 4-(2-pyridyl) piperazine-1-carboxamides: Potent Vanilloid Receptor 1 Antagonists, Bioorg Med Chem Lett 13, 3611-3616, 2003.

Garcia-Martinez, C. et al., Attenuation of Thermal Nociception and Hyperalgesia by VR1 Blockers, Proc. Natl, Acad. Sci. U.S.A. 99, 2374-2379, 2002.

Gunthorpe, M.J. et al., Identification and Characterization of SB-366791, a Potent and Selective Vanilloid Receptor (VR1/TRPV1) Antagonist, Neuropharmacology 46, 133-149,/1s, 2004.

Sathianathan, V. et al., Insulin Induces Cobalt Uptake in a Subpopulation of Rat Cultured Primary Sensory Neurons, Neurosci. Lett. 18, 2477-2486, 2003.

* cited by examiner

INHIBITION OF THE ACTIVITY OF THE CAPSAICIN RECEPTOR IN THE TREATMENT OF OBESITY OR OBESITY-RELATED DISEASES AND DISORDERS

CROSS-REFERENCE TO RELATED APPLICATIONS

This application is a 35 U.S.C. §371 National Stage application of International Application PCT/DK2005/000502, filed Jul. 18, 2005, which claimed priority of Danish Patent Application PA 2004 01126, filed Jul. 19, 2004; this application claims priority under 35 U.S.C. §119 of U.S. Provisional Application 60/589,242, filed Jul. 20, 2004.

FIELD OF THE INVENTION

The present invention is in the field of human medicine, particularly in the treatment of diseases and disorders associated with obesity such as impaired glucose tolerance, insulin resistance and diabetes mellitus. More specifically, the invention relates to a method of treating obesity related diseases and disorders by administering a compound which modulates the activity of the capsaicin receptor.

BACKGROUND OF THE INVENTION

Obesity and its related disorders is becoming a very serious and world wide health problem. The prevalence of obesity and its related disorders is increasing epidemically, and is associated with a major reduction in the quality of life for patients and with enormous health care cost for the society[1]. Prevention strategies have not only proven to preserve the functional abilities of potential diabetics, but also to be a national investment with the potential for a significant return[2,3]. Therefore, the implementation of effective intervention strategies seems prudent[4].

Obesity-induced pathology is linked with the development of impaired glucose tolerance due to both impaired insulin secretion and increased insulin resistance. Obesity is associated with a cluster of disorders, such as type 2 diabetes, type 1 diabetes, cardiovascular disease, hypertension, cancer, including but not limited to colon cancer, rectal cancer, colorectal cancer, pancreatic cancer, esophageal cancer, breast cancer, prostate cancer, uterine cancer, kidney cancer, endometrial cancer, gall bladder cancer, thyroid cancer, liver cancer, cervical cancer, ovarian cancer, stomach cancer, non-Hodgkin's lymphoma, multiple myeloma, and reproductive disorders, including but not limited to polycystic ovarian syndrome (PCO), infertility, and impotency or erectile dysfunction. It has been shown, that by reducing the fat in the diet combined with daily exercise, the risk of developing type 2 diabetes can be reduced by 58%[5]. This improvement exceeded the gains observed after pharmacological intervention, such as with metformin. Weight loss programs however, are often not successful over longer periods, and patients tend to regain weight and return to their previous bodyweight after termination of intensive monitoring. Thus, permanently reducing bodyweight, as a preventive measure for obesity-induced disorders, seems increasingly difficult. Presently, only surgical modulation of the gastrointestinal tract has been proven successful for a prolonged period of time. Pharmaceutically, a reduction of bodyweight has been proven difficult; therefore the current treatment of obese patients is aimed at preventing or ameliorating their complications due to obesity. The current conventional therapies are not adequate; therefore alternative ways to prevent the obesity-related disorders are needed.

SUMMARY OF THE INVENTION

The present invention provides a method of treating diseases or disorders benefiting from inactivating or down regulating the activity of the capsaicin receptor in a mammal by administering a therapeutically-effective amount of a direct or indirect capsaicin receptor antagonist.

The present invention also provides a method of treating obesity in a mammal by administering a therapeutically-effective amount of a direct or indirect capsaicin receptor antagonist.

The invention further provides a method for treating obesity-related diseases and disorders in a mammal by inactivating or down regulating the activity of the capsaicin receptor in a mammal by administering a therapeutically-effective amount of a direct or indirect capsaicin receptor antagonist.

The invention further provides a method for treating obesity-related diseases and disorders in a mammal by administering a therapeutically-effective amount of a direct or indirect capsaicin receptor antagonist in combination with one or more further active agents in any suitable ratios. When used in combination with one or more further active agents, the combination of compounds is preferably a synergistic combination. Synergy occurs when the effect of the compounds when administered in combination is greater than the additive effect of the compounds when administered as a single agent. In general, a synergistic effect is most clearly demonstrated at sub-optimal concentrations of the compounds. Such further active agents may be selected from antidiabetic agents, antihyperlipidemic agents, antiobesity agents, antihypertensive agents and agents for the treatment of complications resulting from or associated with obesity or diabetes.

BRIEF DESCRIPTION OF THE DRAWINGS

FIG. 1b shows the areas under the blood glucose curves in FIG. 1a.

DETAILED DESCRIPTION OF THE INVENTION

The present invention provides a method for treating obesity or obesity related diseases or disorders in a mammal in need thereof by inactivating or down regulating the activity of the capsaicin receptor, comprising: administering a therapeutically-effective amount of a direct or indirect capsaicin receptor antagonist.

A further embodiment of the present invention provides a method wherein the obesity-related disease or disorder is selected from the following: type 1 diabetes, type 2 diabetes, impaired glucose tolerance, cardiovascular disease, hypertension, insulin resistance, cancer and reproductive disorders.

A further embodiment of the present invention provides a method wherein the cancer is selected from: colon cancer, rectal cancer, colorectal cancer, pancreatic cancer, esophageal cancer, breast cancer, prostate cancer, uterine cancer, kidney cancer, endometrial cancer, gall bladder cancer, thyroid cancer, liver cancer, cervical cancer, ovarian cancer, stomach cancer, non-Hodgkin's lymphoma, and multiple myeloma.

A further embodiment of the present invention provides a method wherein the reproductive disorder is selected from: polycystic ovarian syndrome (PCO), infertility, and impotency or erectile dysfunction.

A further embodiment of the present invention provides a method wherein the direct or indirect capsaicin receptor antagonist is selected from the following: natural products, synthetic organic compounds, peptides, proteins, antibodies, antibody fragments, single chain antibodies, and antibody based constructs.

A further embodiment of the present invention provides a method wherein a therapeutically-effective amount of a direct or indirect capsaicin receptor antagonist is administered in combination with a further active agent selected from antidiabetic agents, antihyperlipidemic agents, antiobesity agents, and agents for the treatment of complications resulting from or associated with obesity or obesity related diseases or disorders.

In another embodiment of the invention, an article of manufacture, or kit containing materials useful in the presently claimed methods is provided. The article of manufacture comprises a container and a label. Suitable containers include, for example, bottles, vials, syringes, and test tubes. The containers may be formed from a variety of materials such as glass or plastic. The container holds a composition which is effective for specifically inhibiting capsaicin receptor action and may have a sterile access port (for example the container may be an intravenous solution bag or vial having a stopper pierceable by a hypodermic injection needle). The active agent in the composition is a capsaicin receptor antagonist and/or a capsaicin or anandamide neutralizing agent. The label on or associated with, the container indicates that the composition is used for treating obesity and/or related disorders. The article of manufacture may further comprise a second container comprising a pharmaceutically-acceptable buffer, such as phosphate-buffered saline, Ringer's solution and dextrose solution. It may further include other materials desirable from a commercial end user standpoint, including other buffers, diluents, filters, needles, syringes, and package inserts with instruction to use.

A further embodiment of the present invention provides a method for the treatment of conditions where low-grade inflammation is associated with obesity and obesity-related disorders, comprising: administering to a subject in need thereof, a therapeutically-effective amount of a direct or indirect capsaicin receptor antagonist.

Obesity occurs as a result of a positive energy balance when the amount of energy intake exceeds the amount of energy expenditure. Under normal conditions, excess energy is stored as fat. It is believed and to some extent known that several factors from the periphery, for example leptin and insulin, are affected by this process. These factors can affect the process of food intake (and possibly of energy expenditure) and return the energy balance to neutral. This normal feed-back system of controlling energy balance is a protective system that prevents obesity and its related disorders. However, mammals can easily override this feed-back system resulting in obesity-induced diseases and disorders. Obesity-induced disorders are associated with the destabilization of other homeostatic systems, for example glucose or lipid homeostasis, eventually leading to impaired glucose tolerance associated with diminished insulin secretion and increased insulin resistance. The exact mechanisms underlying the obesity-induced disorders are not fully understood.

Obesity-induced pathologies seem to be associated with a low-grade inflammatory state[6-8]. Thus, insulin resistance and the degree of glycemic control (or $HbA_{1c}$) have been associated with increased levels of C reactive protein (a marker of first phase inflammation)[9,10]. Several inflammatory markers have additionally been shown to correlate with percentage body fat in Pima Indians[11], thus suggesting that inflammation might have a role in the pathogenesis of obesity and its related diseases and disorders.

Several factors released or generated following tissue damage or during inflammation are capable of interacting with polymodal sensory afferent nerves. These factors include lipids, hydrogen ions, heat, ATP, serotonin, bradykinin, nerve growth factor and anandamide. They interact with various receptors (including, but not limited to, TRPV1, CB1, PG or P2X3) or ion-channels (including but not limited to ASICS (acid-sensing ion channels)) in the cell-membrane, and/or induce an alteration in the state of intracellular messengers and enzymes (including, but not limited to, ATP and PKC) provoking a cellular influx of calcium and concomitant activation of the nerve fiber. These factors can all act synergistically[12], and most often involve the capsaicin-receptor through direct or indirect activation, to provide a prompt and sufficient reaction to injury. The exogenous vanilloid, capsaicin, has been shown to selectively bind to this subset of nerve fibers via the capsaicin receptor.

Capsaicin-sensitive nerves are sensory nerve fibers that transmit afferent signals from the periphery regarding noxious stimuli[13], satiety[14] and temperature[15]. The sensory afferent nerves of the Aδ and C fiber types are both involved in nociception, are heat-sensitive and are able of responding to the exogenous vanilloid, capsaicin. Capsaicin has thus been used as a pharmacological tool to investigate the role of these fibers.

The use of capsaicin to investigate the role of the capsaicin-sensitive nerves in laboratory mammals has been carried out for decades, especially to study their role in pain. Nearly 40 years ago, capsaicin, the pungent ingredient of red hot chili pepper, was shown to selectively activate a subset of primary afferent nerves, the Aδ and C fiber types. The mechanism by which this occurred was not known at that time. By administering capsaicin systemically to a mammal, an acute stimulation occurs due to the influx of cations into the nerve cell, depolarization, increased excitability and the generation of action potentials. This elicits an afferent effect, as well as an efferent signal consisting of the release of vasoactive and pro-inflammatory peptides (e.g. CGRP, somatostatin and Substance P). The magnitude of these signals is related to the degree of stimulation/injury underlying the interaction with the nerve fibers. The fact that stimulation of the receptor by capsaicin allows the influx of calcium makes capsaicin a neurotoxin when administered at high doses. Capsaicin administered at neurotoxic doses elicits a permanent (when given to neonatal laboratory mammals) or a transient and reversible desensitization of the capsaicin-sensitive nerves (when given to adult mammals). The desensitized state permits the investigation of the role of the capsaicin-sensitive nerves in normal or diseased states in laboratory mammals. The desensitized state, however does not rule out which factor is responsible for a possible change of condition. Any receptor, ion-channel, intracellular substance or extracellular factor, with the potential to interact with the capsaicin-sensitive nerves, could theoretically be responsible for the desensitized effect—alone or in combination.

A number of direct capsaicin analogues have been identified (such as resiniferatoxin, RTX[16,17] or olvanil[18,19] and cannabinoids[20]. Indirect activation of the capsaicin receptor can also occur for example through the activation of intracellular PKC[21] and therefore compounds including but not limited to PKC activators are considered to be indirect capsaicin agonists. Capsaicin antagonists have also been identified (such as capsazepine or ruthenium red) but have been of little functionality in in vivo experiments. Recently, the capsaicin receptor antagonist N-(4-tertiarybutylphenyl)-4-(3-chloro-pyridin-2-yl)tetrahydropyrazine-1(2H)-carbox-amide (BCTC) has been shown effective with regard to inhibiting capsaicin-mediated hyperalgesia, inflammatory hyperalgesia or allodynia, and hyperalgesia after nerve injury[22,23].

The role of the capsaicin sensitive nerves in normal energy balance has been investigated through experimental studies using capsaicin desensitization. It was found that capsaicin sensitive nerves have an effect on food intake[14], temperature regulation[15] and glucose homeostasis through altered insulin secretion[24] and insulin sensitivity[25].

In laboratory animal models of obesity and its related disorder type 2 diabetes, we have recently shown that desensitization by means of capsaicin or RTX improves glycemic control, including blood glucose levels and $HbA_{1c}$[26,27], dyslipidemia[27], the activity of plasma dipeptidyl peptidase IV (DPP IV)[28], insulin secretion[29] and insulin sensitivity[30]. These findings suggest the system of capsaicin-sensitive nerves is overactive during obesity or obesity-related disorders. Down-regulation of capsaicin-sensitive nerves could be a novel pharmacological way of treating obesity and obesity-related disorders.

It has been shown that capsaicin binds to a specific receptor, the capsaicin receptor. This receptor, also called the vanilloid receptor 1 (VR1) or transient receptor channel vanilloid 1 (TRPV1), was cloned and described several years ago[31,32]. The capsaicin receptor is found in the membrane of peripheral sensory afferent nerves and in various brain regions such as hypothalamus, hippocampus and substantia nigra[33]. The receptor is also found on non-neuronal cells like mast cells, keratinocytes, white blood cells, and macrophages[34]. The endogenous ligand for the capsaicin receptor has not yet been identified, although ligands from the fatty acid and eicosonoid pools, such as anandamide, have been convincingly suggested[35].

Two research groups have generated and characterized knock-out mice lacking the capsaicin receptor. The mice were found to be severely deficient in their responses to chemical or thermal sensitivity[36], and although the mice appeared normal in a wide range of behavioral tests, including responses to acute noxious thermal stimuli, their ability to develop carrageenan-induced thermal hyperalgesia was completely absent[37]. These data suggest that the capsaicin receptor is required for inflammatory sensitization to noxious thermal stimuli, and that alternative mechanisms exist that are sufficient for normal sensation of noxious heat.

Glucose intolerance can be induced by a high-fat diet in normal mice and is, in early phases, solely explained by reduced glucose effectiveness, whereas insufficient early insulin secretion is of importance after long-term feeding[38].

The present invention details the surprising discovery that in the capsaicin receptor knock-out mice, the state of impaired glucose tolerance after a period on high-fat diet was improved in the mice lacking the capsaicin receptor, and that this was associated with a potentiated insulin response to glucose. Thus, the capsaicin receptor is involved in mediating the high-fat induced glucose intolerance partly through reducing glucose-stimulated insulin secretion. Consequently, erasing, blocking or antagonizing the capsaicin receptor action ameliorates the consequences of obesity and could accordingly be used as a novel treatment for obesity and disorders related thereto.

Glucose tolerance can vary from hour to hour[39], but is generally constant in normal individuals. In obesity or obesity-related disorders, glucose intolerance, due to decreased insulin secretion or insulin sensitivity, is present. According to World Health Organization criteria, glucose intolerance (IGT) is characterized by two hour plasma glucose values between 7.8 and 11.0 mM following a standard oral glucose tolerance test (OGTT).

As used herein, "treating" or "treatment" describes the management and care of a patient for the purpose of combating the disease, condition, or disorder. Treating includes the administration of a compound of the present invention to prevent the onset of the symptoms or complications, alleviating the symptoms or complications, or eliminating the disease, condition, or disorder. Treating impaired glucose tolerance therefore includes the inhibition of rise in blood glucose following a standard oral glucose tolerance test, possibly in association with improved insulin secretion and/or insulin sensitivity.

As employed herein, the term "obesity" implies an excess of adipose tissue. In this context, obesity is best viewed as any degree of excess adiposity that imparts a health risk. The distinction between normal and obese individuals can only be approximated, but the health risk imparted by obesity is probably a continuum with increasing adiposity. However, in the context of the present invention, individuals with a Body Mass Index (BMI=body weight in kilograms divided by the square of the height in meters) above 25 are to be regarded as obese.

As used herein, the term "related disorders" includes but is not limited to type I diabetes, type 2 diabetes, cardiovascular disease, cancer, and other disease states whose etiology stems from or is associated with obesity.

The term "low-grade inflammation" as employed herein refers to a condition characterised by subtle increase of inflammatory markers to a degree that is far below that seen in acute infections. Inflammatory markers include, but are not limited to, C reactive protein, serum amyloid A protein, leucocyte count, cytokines (e.g. IL-6, IL-8 and TNF-alpha) and neuropeptides (e.g. CGRP). For further information with regard to the relationship between obesity and inflammation, reference may be made to an article by Ramos et al. in *Surgery*, 134(2), pp. 329-335 (2003), and references cited therein.

The term "administering" or "administration", as used herein encompasses any means for introducing a capsaicin-receptor antagonist or antibody to capsaicin or capsaicin analogues (both direct and indirect) into the body such that the substance is able to interact with the capsaicin receptor or with capsaicin or capsaicin analogues. Preferred routes of administration will introduce the substance into the systemic circulation. Examples include, but are not limited to, oral administration, as well as transdermal, subcutaneous, intravenous and intramuscular injection.

The active agents employed in the context of the present invention are administered to a mammal, preferably a human, in accordance with known methods, such as intravenous administration as a bolus, or by continuous infusion over a period of time, or by intramuscular, intraperitoneal, intracerebral, intracerebrospinal, subcutaneous, intra-articular, intrasynovial, intrathecal, intraocular, intralesional, oral, topical or pulmonary (i.e. by inhalation) administration, or via sustained release.

A "therapeutically-effective" amount is at least the minimal dose, but less than a toxic dose, of an active agent which is necessary to impart therapeutic benefit to a mammal. Stated another way, a therapeutically-effective amount is an amount which induces, ameliorates or otherwise causes an improvement in the glucose intolerant state of the mammal.

"Carriers" as used herein include pharmaceutically-acceptable carriers, excipients, or stabilizers which are non-toxic to the cell or mammal being exposed thereto at the dosages and concentrations employed. Often the physiologically-acceptable carrier is an aqueous pH buffered solution. Examples of physiologically acceptable carriers include buffers such as phosphate, citrate and other organic acids; antioxidants including ascorbic acid; low molecule weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counter ions such as sodium; and/or nonionic surfactants such as TWEEN®, polyethylene glycol (PEG), and PLURONICS®.

The term "combination therapy", "combined", "in combination with", and the like, as used herein refers to the administration of a single pharmaceutical dosage formulation which comprises the a capsaicin-receptor antagonist or antibody to capsaicin or capsaicin analogue compound of the present invention and another active agent(s), as well as administration of each active agent(s) in its own separate pharmaceutical dosage formulation. Where separate dosage formulations are used, the compound of the present invention and another active agent(s) can be administered to the patient at essentially the same time, i.e. concurrently, or at separate staggered times, i.e. sequentially. When given by different dosage formulations, the route of administration may be the same or different for each agent. Any route of administration known or contemplated for the individual agents is acceptable for the practice of the present invention.

The term "mammal" as used herein refers to any animal classified as a mammal, including humans, domestic farm and zoo animals, and sports or companion animals, etc. In a preferred embodiment of the invention, the mammal is a human.

The term "antibody" is used in the broadest sense and specifically includes monoclonal antibodies, chimeric antibodies, humanized antibodies, and fully human antibodies.

The term "monoclonal antibody" as used herein refers to an antibody obtained from a population of substantially homogenous antibodies, i.e., the individual antibodies comprising the population are identical except for possible naturally-occurring mutations that may be present in minor amounts.

"Antibody fragments" refers to a portion of an intact antibody, preferably the antigen binding or variable region of the intact antibody. Examples of antibody fragments include Fab, Fab', F(ab')1 and Fv fragments; diabodies: linear antibodies; single-chain antibody molecules; and multispecific antibodies formed from antibody fragments.

The term "Fv" is the minimum antibody fragment which contains a complete antigen-recognition and binding site. This region consists of a dimer of one heavy- and one light chain variable domain in tight, non-covalent association. It is in this configuration that the three complementarity-determining regions (CDRs) of each variable domain interact to define an antigen-binding site on the surface of the VH-VL dimer. Collectively, the six CDRs confer antigen-binding specificity to the antibody. However, even a single variable domain (or half of an Fv comprising only three CDR specific for an antigen) has the ability to recognize and bind antigen, although at a lower avidity than a complete antibody.

The Fab fragment also contains the constant domain of the light chain and the first constant domain (CHI) of the heavy chain. Fab fragments differ from Fv fragments by the addition of a few residues at the carboxy terminus of the heavy chain CHI domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

Papain digestion of antibodies produces two identical antigen-binding fragments, called Fab fragments, each with a single antigen-binding site, and a residual Fc fragment, a designation reflecting the ability to crystallize readily. Pepsin treatment yields an $F(ab')_2$ fragment that has two antigen-combining sites and is still capable of crosslinking antigen.

The "light-chains" of antibodies (immunoglobulins) from any vertebrate species can be assigned to one of two clearly distinct types, called kappa and lambda, based on the amino acid sequences of their constant domains. Depending on the amino acid sequence of the constant domain of their heave chains, immunoglobulins can be assigned to different classes. There are five major classes of immunoglobulins IgA, IgD, IgE, IgG, and IgM, and several of these may be further divided into subclasses (isotypes), e.g. IgG1, IgG2, IgG3, IgA and IgA2.

"Single-chain Fv" antibody fragments comprise the VH and VL domains of antibody, wherein these domains are present in a single polypeptide chain. Preferably, the Fv polypeptide further comprises a polypeptide linker between the VH and VL domain, which enables the sFv to form the desired structure for antigen binding. The term "immunoadhesion" designates antibody-like molecules that combine the binding specificity of a heterologous protein (an 'adhesion') with the effector functions of immunoglobulin constant domains. Structurally, the immunoadhesions comprise a fusion of an amino acid sequence with the desired binding specificity which is other than the antigen recognition and binding site of an antibody (i.e. is heterologous), and an immunoglobulin constant domain sequence in the immunoadhesion may be obtained from any immunoglobulin such as IgG-1, IgG-2, IgG-3 or UgG4 subtypes, IgA (including IgA-1 and IgA-2), IgE, IgD or IgM.

The term "diabodies" refers to small antibody fragments with two antigen-binding sites, which fragments comprise a heavy-chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen binding sites.

A "capsaicin receptor antagonist" is any compound that partially or fully antagonizes, blocks, or otherwise inhibits the biological action of the endogenous capsacin receptor ligand, capsaicin or capsaicin analogues by binding to the capsaicin receptor (direct antagonist) or by blocking the activating stimulus (indirect antagonist/allosteric antagonist) without causing stimulation, e.g. influx of calcium into the cell. Examples of compounds that are receptor antagonists without agonist activity (no stimulation of calcium influx into the cell) are halogenated analogs of RTX[43,44]), diaryl piperazines and related compounds[45], N-(3-acyloxy-2-benzylpropyl)-N'-[4-(methylsulfonylamino)benzyl]-thiourea analogues[46] KJM429 [N-(4-tert-butylbenzyl)-N'-[4-(methylsulfonylamino)benzyl]thiourea] and JYL1421 [N-(4-tertbutylbenzyl)-N'-[3-fluoro-4-(methylsulfonylamino) benzyl]thiourea][47] N-(4-chlorobenzyl)-N'-(4-hydroxy-3-iodo-5-methoxybenzyl) thiourea (IBTU)[48], acyclic phenethylthiocarbamate derivatives[49], (urea derivatives and others[50-52], amine derivatives[53], pyridine derivatives[54], urea and amid derivatives[55,56], BCTC[22 23], N-alkylglycines[57], SB-366791 (N-(3-methoxyphenyl)-4-chlorocinnamide)[58], and the like. Compounds including, but not limited to, these examples are thus consistent with various embodiments of the present invention.

Direct capsaicin receptor antagonists or indirect capsaicin receptor antagonists are compounds useful in the presently claimed method and include but are not limited to natural products, synthetic organic compounds, peptides, proteins, antibodies, antibody fragments, single chain antibodies, and antibody based constructs.

The current level of skill in the art of receptor binding and capsaicin receptor assays places capsaicin receptor antagonists well within the grasp of the ordinarily skilled artisan. There are several routine approaches for identifying a capsaicin receptor antagonist. One basic scheme involves a receptor binding assay followed by measurement of calcium influx into the cell harboring the receptor. This is accomplished using routine radiometric binding methods. Characterization can also be performed using functional tests on cells expressing the VR1 receptor (clonal cell line or dorsal root ganglion cell) in order to evaluate whether they inhibit the cellular influx of calcium provoked by an agonist (e.g. capsaicin, low pH or elevated temperatures (>45° C.)). Determination of calcium influx can be made by using fluorescent calcium dyes (e.g. FURA-2), radioactive calcium, or by patch clamp techniques. Compounds that bind or by them selves do not stimulate the cellular influx of calcium are considered as antagonists. The in vivo effects of such compounds may be evaluated by various pain related tests such as their ability to counteract the pain/hyperalgesia elicited by intraplantar injection of capsaicin in a rodent paw.

Cellular based assays can by used to identify indirect capsaicin receptor agonists[59] and therefore also their antagonists.

Antibody-based capsaicin-receptor antagonists are also consistent with the claimed method. Anti-capsaicin receptor antibodies may be generated by a variety of well-known methods that include traditional antisera production and monoclonal antibody techniques. Modified antibody forms described above may then be produced using established techniques. Once generated, the antibodies are checked for capsaicin receptor antagonist activity in the manner described above.

Neutralizing agents of capsaicin or its direct or indirect analogues represent other aspects of the invention. In this embodiment, capsaicin or its direct or indirect analogues are neutralized or otherwise rendered biologically inactive thereby not being able to affect the receptor. Agents suitable for this application are those which specifically bind capsaicin or its direct or indirect analogues, preferably with a higher affinity constant than that of the capsaicin receptor.

Antibody or antibody-based agents are preferred because they can be purposefully generated using well established techniques.

Immunoadhesions (Fc fusion constructs, similar to ENBREL®, where the soluble ligand-binding domain of the capsaicin-receptor is fused to human Fc) are also consistent with this aspect of the invention.

Dosage and Formulation

A suitable direct or indirect capsaicin receptor antagonist can be administered to patients to treat obesity and other related diseases and disorders as the compound alone and or mixed with an acceptable carrier in the form of pharmaceutical formulations. Those skilled in the art of treating obesity and other related diseases and disorders can easily determine the dosage and route of administration of the compound to mammals, including humans, in need of such treatment. Dosages and desired drug concentration for pharmaceutical compositions of the present invention may vary depending on the particular use envisioned. Animal experiments provide reliable guidance for the determination of effective doses for human therapy.

The route of administration may include but is not limited to oral, intraoral, rectal, transdermal, buccal, intranasal, pulmonary, subcutaneous, intramuscular, intradermal, sublingual, intracolonic, intraoccular, intravenous, or intestinal administration. The compound is formulated according to the route of administration based on acceptable pharmacy practice (Fingl et al., in *The Pharmacological Basis of Therapeutics*, Ch. 1, p. 1, 1975; *Remington's Pharmaceutical Sciences*, 18th ed., Mack Publishing Co, Easton, Pa., 1990).

The pharmaceutically acceptable direct or indirect capsaicin receptor antagonist composition of the present invention can be administered in multiple dosage forms such as tablets, capsules (each of which includes sustained release or timed release formulations), pills, powders, granules, elixirs, in situ gels, microspheres, crystalline complexes, liposomes, microemulsions, tinctures, suspensions, syrups, aerosol sprays and emulsions. The composition of the present invention can also be administered in oral, intravenous (bolus or infusion), intraperitoneal, subcutaneous, transdermally or intramuscular form, all using dosage forms well known to those of ordinary skill in the pharmaceutical arts. The composition may be administered alone, but generally will be administered with a pharmaceutical carrier selected on the basis of the chosen route of administration and standard pharmaceutical practice.

The dosage regimen for the composition of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disease state.

By way of general guidance, the daily oral dosage of the active ingredient, when used for the indicated effects, will range between about 0.001 to 1000 mg/kg of body weight, preferably between about 0.01 to 100 mg/kg of body weight per day, and most preferably between about 0.6 to 20 mg/kg/day. Intravenously, the daily dosage of the active ingredient when used for the indicated effects will range between 0.001 ng to 100.0 ng per min/per Kg of body weight during a constant rate infusion. Such constant intravenous infusion can be preferably administered at a rate of 0.01 ng to 50 ng per mm per Kg body weight and most preferably at 0.1 ng to 10.0 mg per mm per Kg body weight. The composition of this invention may be administered in a single daily dose, or the total daily dosage may be administered in divided doses of two, three, or four times daily. The composition of this invention may also be administered by a depot formulation that will allow sustained release of the drug over a period of days/weeks/months as desired.

The composition of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The composition is typically administered in a mixture with suitable pharmaceutical diluents, excipients, or carriers (collectively referred to herein as pharmaceutical carriers) suitably selected with respect to the intended form of administration, that is, oral tablets, capsules, elixirs, aerosol sprays generated with or without propellant and syrups, and consistent with conventional pharmaceutical practices.

For instance, for oral administration in the form of a tablet or capsule, the active drug component can be combined with an oral, non-toxic, pharmaceutically acceptable, inert carrier such as but not limited to, lactose, starch, sucrose, glucose, methyl cellulose, magnesium stearate, dicalcium phosphate, calcium sulfate, mannitol, and sorbitol; for oral administration in liquid form, the oral drug components can be combined with any oral, non-toxic, pharmaceutically acceptable inert carrier such as, but not limited to, ethanol, glycerol, and water. Moreover, when desired or necessary, suitable binders, lubricants, disintegrating agents, and coloring agents can also be incorporated into the mixture. Suitable binders include, but not limited to, starch, gelatin, natural sugars such as, but not limited to, glucose or beta-lactose, corn sweeteners, natural and synthetic gums such as acacia, tragacanth, or sodium alginate, carboxymethylcellulose, polyethylene glycol, and waxes. Lubricants used in these dosage forms include sodium oleate, sodium stearate, magnesium stearate, sodium benzoate, sodium acetate, and sodium chloride. Disintegrants include, but are not limited to, starch, methyl cellulose, agar, bentonite, and xanthan gum.

The composition of the present invention may also be administered in the form of mixed micellar or liposome delivery systems, such as small unilamellar vesicles, large unilamellar vesicles, and multilamellar vesicles. Liposomes can be formed from a variety of phospholipids, such as cholesterol, stearylamine, or phosphatidyicholines. Permeation enhancers may be added to enhance drug absorption.

Since prodrugs are known to enhance numerous desirable qualities of pharmaceuticals (i.e., solubility, bioavailability, manufacturing, etc.) the compounds of the present invention may be delivered in prodrug form. Thus, the present invention is intended to cover prodrugs of the presently claimed compounds, methods of delivering the same and compositions containing the same.

The compositions of the present invention may also be coupled with soluble polymers as targetable drug carriers. Such polymers can include polyvinyl-pyrrolidone, pyran copolymer, polyhydroxypropyl-methacrylamide-phenol, polyhydroxyethylaspartamidephenol, or polyethyleneoxide-polylysine substituted with palmitoyl residues. Furthermore, the composition of the present invention may be combined with a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Dosage forms (pharmaceutical compositions) suitable for administration may contain from about 0.1 milligram to about 500 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivative, magnesium stearate, and stearic acid. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solution for parenteral administration preferably contains a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington: The Science and Practice of Pharmacy*, Nineteenth Edition, Mack Publishing Company, 1995, a standard reference text in this field Representative useful pharmaceutical dosage forms for administration of the compound of this invention can be illustrated as follows:

Capsules

A large number of unit capsules can be prepared by filling standard two-piece hard gelatin capsules with 100 milligrams of powdered active ingredient, 150 milligrams of lactose, 50 milligrams of cellulose, and 6 milligrams magnesium stearate.

Soft Gelatin Capsules

A mixture of active ingredient in digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit, for example is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring for example, 1.5% by weight of active ingredient in 10% by volume propylene glycol and water. The solution should be made isotonic with sodium chloride and sterilized.

Suspension

An aqueous suspension can be prepared for oral and/or parenteral administration so that, for example, each 5 mL contains 100 mg of finely divided active ingredient, 20 mg of sodium carboxymethyl cellulose, 5 mg of sodium benzoate, 1.0 g of sorbitol solution, U.S.P., and 0.025 mL of vanillin or other palatable flavoring.

Biodegradable Microparticles

A sustained-release parenteral composition suitable for administration by injection may be prepared, for example, by dissolving a suitable biodegradable polymer in a solvent, adding to the polymer solution the active agent to be incorporated, and removing the solvent from the matrix thereby forming the matrix of the polymer with the active agent distributed throughout the matrix.

All references, including publications, patent applications, and patents, cited herein are hereby incorporated by reference to the same extent as if each reference were individually and specifically indicated to be incorporated by reference and were set forth in its entirety herein (to the maximum extent permitted by law). Any combination of the above-described elements in all possible variations thereof is encompassed by the invention unless otherwise indicated herein or otherwise clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising," "having," "including," and "containing" are to be construed as open-ended terms (i.e., meaning "including, but not limited to,") unless otherwise noted and should be read as encompassing the phrases "consisting", "substantially comprised of," and "consisting essentially of" (e.g., where a disclosure of a composition "comprising" a particular ingredient is made, it should be understood that the invention also provides an otherwise identical composition characterized by, in relevant part, consisting essentially of the ingredient and (independently) a composition consisting solely of the ingredient).

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

EXAMPLES

The following examples are offered for illustrative purposes only, and are not intended to limit the scope of the present invention in any way.

The capsaicin receptor (VR1) antagonist BCTC (vide supra) employed as described below may be synthesized as described in WO 02/08221.

Example 1

Laboratory animals: Male (n=11) capsaicin receptor (VR1) knock out mice (Strain name: B6.129S4-Trpv1$^{tm1Jul}$, Stock Number: 003770) and male control mice (n=8) were purchased from Jackson Laboratories, Bar Harbor, Me., U.S. The mice were transported to Denmark at the age of 5 weeks and were kept under ambient controlled conditions on a normal day light cycle (lights on at 6 am, lights off at 6 pm) at the Måløv Animal Unit at Novo Nordisk A/S, Denmark from then and until the age of 29 weeks of age. The mice were kept in groups (one group per cage) in standard cages (Eurostandard Type IV, Techniplast, Scanbur, Denmark) and were given free access to acidified (0.4% citric acid) tap water and standard chow (Altromin, Brogaarden Aps, Denmark). The cages were supplied with wooden wool (Brogaarden, Denmark) as nesting material and the bedding material was aspen chips (Brogaarden, Denmark), changed twice per week as was the bottles of acidified water. At the age of 11 weeks, the chow was changed to a high fat diet (Research Diet Prod. No. D12309, Research Diet Inc, New Brunswick, U.S.).

Oral Glucose Tolerance Test (OGTT)

After 15 weeks on the high fat diet, an OGTT was performed. The mice were fasted for 18 hours prior to the OGTT. Fasting blood glucose was determined as described below where after glucose at a concentration of 500 mg/ml (Sygehus apotekerne, Denmark) was given orally by gavage (2 g/kg po). Blood samples for the determination of blood glucose were obtained from the tail tip capillary of conscious mice. Blood was collected in heparinized 5 µl capillary tubes and immediately suspended in 250 µl EBIO buffer (EBIO, Eppendorf, Germany). Following the experiment, glucose was determined using the glucose oxidase method (EBIO, Eppendorf, Germany). The area under the blood glucose curves (AUC) was determined by the trapezoidal method. The mean of the two groups were compared by use of the Student's t-test method. P<0.05 was considered to be a statistically significant difference.

Figure 1A:
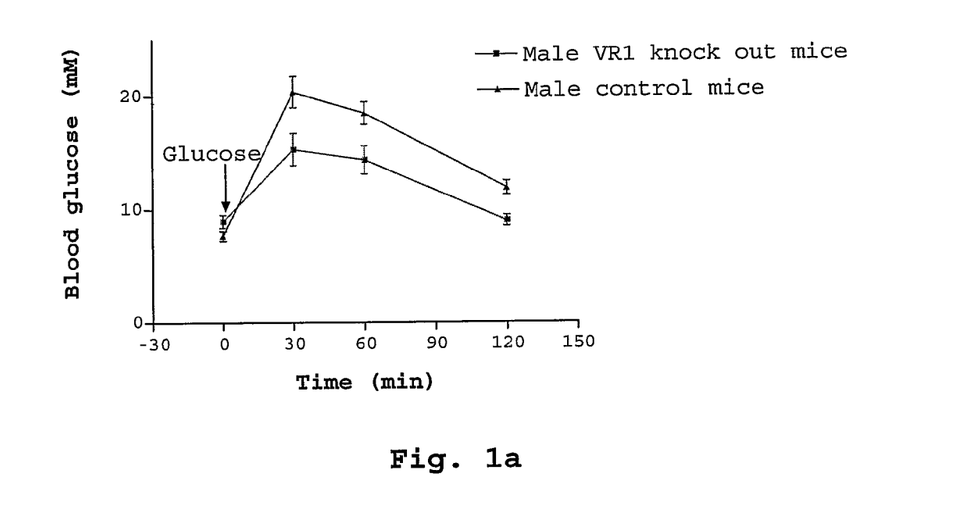
FIG. 1a shows the 0-120 min blood glucose curves after an oral glucose tolerance test (OGTT) of 2 g/kg p.o. in 15-week old high-fat-fed male capsaicin receptor (VR1) knock-out mice and control mice, respectively.

FIG. 1 shows the 0-120 min blood glucose curves (a) after an oral glucose tolerance test (OGTT) of 2 g/kg po in 15 week high fat fed male capsaicin receptor (VR1) knock-out or control mice. The male control mice (triangle up) shows a marked increase in glucose levels following the oral glucose load with blood glucose levels 120 min after the glucose load still elevated above baseline (fasting blood glucose values at time 0 min) suggesting a delayed glucose clearance from the blood, i.e. impaired glucose tolerance. The male VR1 knockout mice (square) shows in comparison a diminished rise in blood glucose and a 120 min blood glucose level back to baseline (fasting blood glucose at time 0 min) thus resembling blood glucose levels in a normal mouse (not on high fat diet) after an OGTT, i.e. normal glucose tolerance.

Figure 1B:
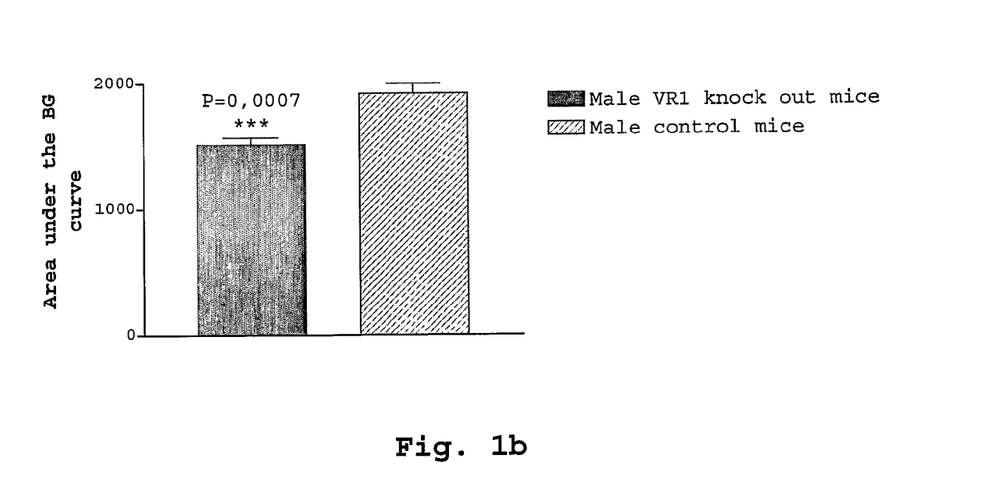

The group mean of the calculated area under the curve of the blood glucose curves (b) shows that during the test period of 120 min, the overall blood glucose levels were highly statistically significantly decreased in the VR1 knock-out mice (filled bar) as compared to the control mice (hatched bar) and proves that glucose intolerance is significantly less pronounced in VR1 knock-out mice as compared to controls after a 15 week period of high fat diet. Down-regulation of the capsaicin receptor could thus be a pharmacological approach in the prevention and treatment of impaired glucose tolerance and its related disorders.

Glucose (ip) Stimulated Early Insulin Secretion

After 18 weeks on high fat diet, the insulin secretion of the mice was tested by injecting glucose intraperitoneally. The mice were fasted for 18 hours prior to the test. Glucose at a concentration of 500 mg/ml (Sygehus apotekerne, Denmark) was given intraperitoneally by injection (2 g/kg i.p.). The assessment of early insulin response to i.p. glucose was assessed 2 min after exposure by sampling app. 70 µl blood from the tail tip capillary of conscious mice into heparinized 100 µl capillary tubes. These tubes were spun (4000 rpm/min/4° C.) and the 15 µl plasma preserved and stored at −20° C. until analysis using an in house ELISA. The mean 2-min plasma insulin levels of the two groups was compared by the nonparametric Mann-Whitney U test due to a statistically significant difference between the variances of the groups. P<0.05 was considered to be a statistically significant difference.

Figure 2:
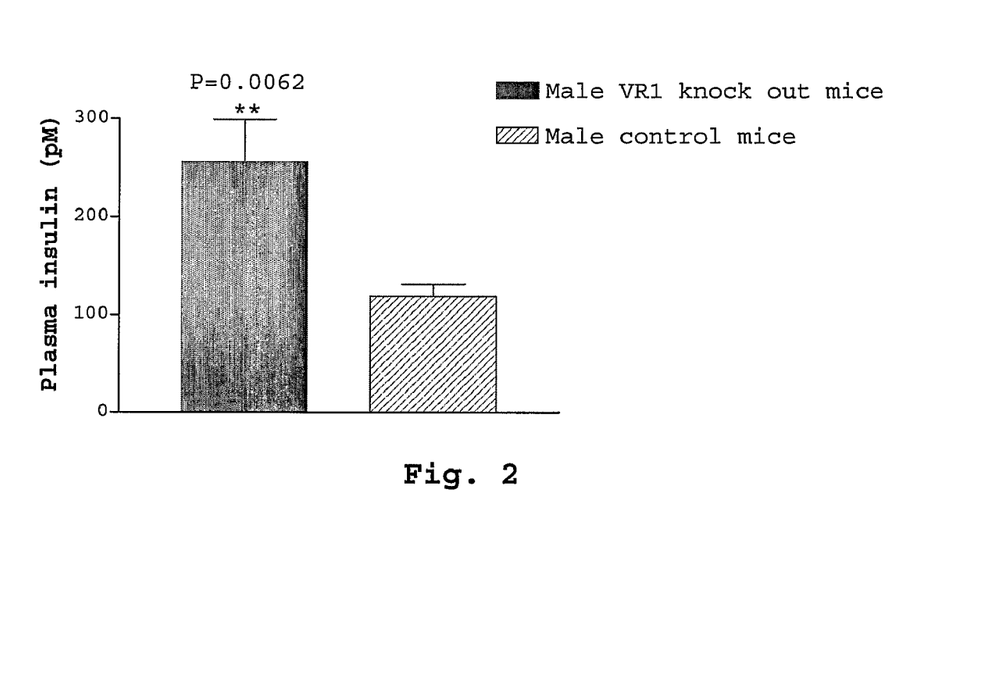
FIG. 2 shows the group means of the plasma insulin levels 2 min after administration of glucose (2 g/kg) i.p. to male VR1 knock-out mice and control mice, respectively.

FIG. 2 shows the group means of the plasma insulin levels 2 min after glucose (2 g/kg) i.p. The VR1 knock-out mice (filled bar) display a significantly higher plasma insulin level 2 min after the glucose load as compared to the control mice (hatched bar). This suggests that the VR1 knock-out mice does not as readily as the control mice develop high fat diet induced impaired insulin secretion. Retention of the ability to secrete insulin in response to glucose could partially explain the normal glucose tolerance in the high fat fed VR1 knockout mice. This suggests that inactivating or down regulating the activity of the capsaicin receptor could be useful as novel pharmacological approach in preventing or treating impaired early insulin secretion.

Example 2

Laboratory animals: Male (n=19) Zucker obese rats were purchased from Charles River Laboratories, U.S. The rats were transported to Denmark at the age of 6 weeks and were kept under ambient controlled conditions on a normal day light cycle (lights on at 6 am, lights off at 6 pm) at the Måløv Animal Unit at Novo Nordisk A/S, Denmark from then and until the age of 9 month of age. The rats were kept in groups of 3 rats per cage until the end of the experiment in standard cages (Eurostandard Type IV, Techniplast, Scanbur, Denmark) and were given free access to acidified (0.4% citric acid) tap water and standard chow (Altromin, Brogaarden Aps, Denmark). The cages were supplied with wooden wool (Brogaarden, Denmark) as nesting material and the bedding material was aspen chips (Brogaarden, Denmark), changed twice per week as was the bottles of acidified water.

Oral Glucose Tolerance Test (OGTT) and Glucose Stimulated Insulin Secretion

At 6 month of age, an OGTT was performed shortly after administering a capsaicin receptor antagonist (BCTC) orally. The rats were fasted for 18 hours prior to the OGTT. Fasting blood glucose and plasma insulin was determined as described below. At time −30 min, BCTC at 15 mg/kg (n=10) or vehicle (n=9) was given orally by gavage. The rats were left in the cage until time 0 where blood glucose was assessed followed by the OGTT. In brief, glucose at a concentration of 500 mg/ml (Sygehus apotekerne, Denmark) was given orally by gavage (2 g/kg po). Blood glucose and plasma insulin was determined at time 30, 60 and 120 min after glucose. Blood samples for the determination of blood glucose and plasma insulin were obtained from the tail tip capillary of conscious, rats. Blood for the measurement of blood glucose was collected in heparinized 5 µl capillary tubes and immediately suspended in 250 µl EBIO buffer (EBIO, Eppendorf, Germany). Following the experiment, glucose was determined using the glucose oxidase method (EBIO, Eppendorf, Germany).

Blood for the analysis of plasma insulin was obtained by sampling app. 70 µl blood from the tail tip capillary of conscious rats into heparinized 100 µl capillary tubes. These tubes were spun (4000 rpm/min/4° C.) and the 15 µl plasma preserved and stored at −20° C. until analysis using an in house ELISA.

Figure 3A:
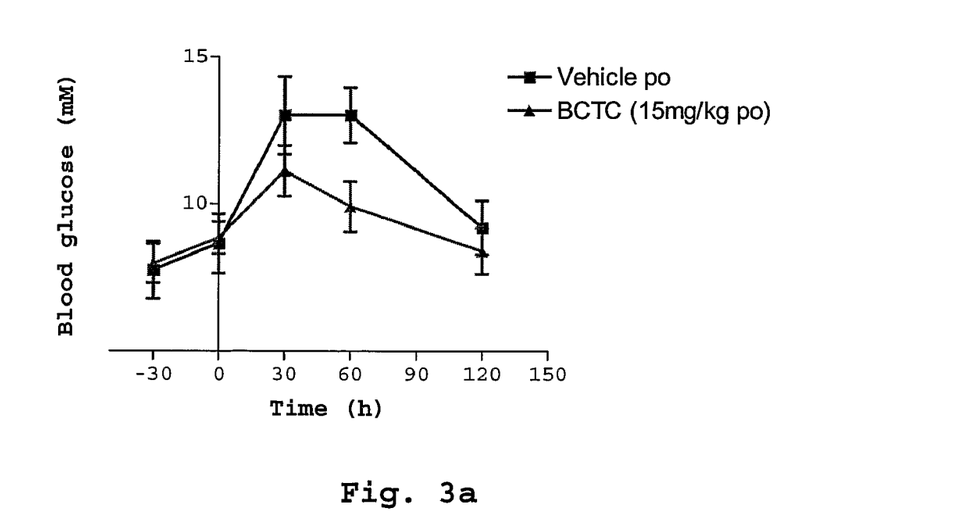
FIG. 3a and FIG. 3b show the −30-120 min blood glucose curves and plasma insulin curves, respectively, after an oral glucose tolerance test (OGTT) of 2 g/kg p.o. in 21-week old Zucker obese rats. The capsaicin receptor antagonist BCTC was administered (15 mg/kg) p.o. at time −30 min, and the glucose load was given at time 0.
Figure 3B:
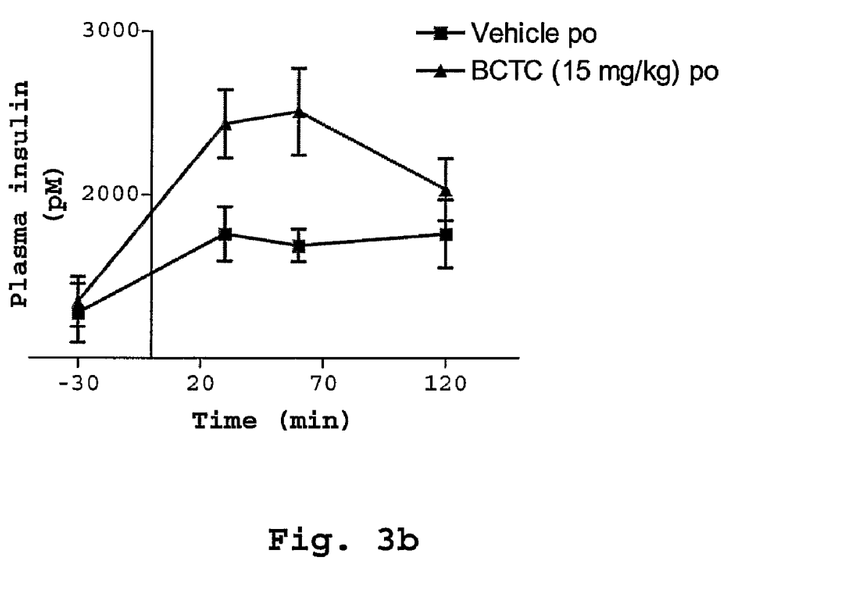

FIG. 3 shows the blood glucose curves (a) and plasma insulin curves (b) after oral dosing of the capsaicin receptor antagonist, BCTC, to 6 month old male Zucker obese rats at time −30 min followed by an oral glucose tolerance test (OGTT) of 2 g/kg po at time 0. The vehicle treated rats (square) shows a marked increase in glucose levels (a) following the oral glucose load suggesting a delayed glucose clearance from the blood, i.e. impaired glucose tolerance. The BCTC treated rats (triangle up) shows in comparison a diminished rise in blood glucose (a) thus displaying improved oral glucose tolerance. The vehicle treated rats (square) further show a reduced glucose stimulated insulin response (b) whereas the BCTC treated rats show considerable higher levels of insulin in plasma after the oral glucose load (b). This suggests that the improvement of oral glucose tolerance in Zucker rats after the treatment with the capsaicin receptor antagonist BCTC is in part mediated via improvement of insulin secretion. These data therefore confirm that the capsaicin receptor is involved in impaired glucose tolerance and impaired glucose stimulated insulin secretion.

Down-regulation of the capsaicin receptor could thus be a pharmacological approach in the prevention and treatment of impaired glucose tolerance and its related disorders and in preventing or treating impaired early insulin secretion.

Measurement of Inflammatory Markers in Mesenteric Adipose Tissue

At 9 months of age, the same rats were tested re. mesenteric inflammatory mediators. The rats were fasted for 18 hours where after they were given BCTC at 15 mg/kg (n=10) or vehicle (n=9) orally by gavage. One hour after treatment, the rats were anaesthetized in isoflurane and decapitated. The mesenteric adipose tissue was quickly removed and transferred to 10× volume pre-chilled RNAlater (Sigma-Aldrich, USA) and stored at −20° C. To prevent area to area effect on gene expressions patterns, 0, 5-1 g tissue was homogenized in TRIzol Reagent (1 ml/100 mg tissue) (TRIzol; Invitrogen Corp.). Total RNA was extracted from 200 ml homogenate according to Qiagene protocol (Qiagene RNeasy Mini handbook, 2001). First-strand cDNA was synthesized using SuperScript III reverse transcriptase and random hexamer primers as described in the manufacturer's protocol (Invitrogen Corp.). cDNA of unknown samples were diluted 1:12 in nuclease-free water (Qiagen Inc.). Samples from each cDNA pool were mixed and diluted 1:6, 1:12, 1:24, 1:48, 1:96, 1:192 and 1:384 in order to create a standard curve for calculation of PCR efficiency, where only PCR efficiency of 100% (±1%) and $R^2$ between 0.99 and 1 were accepted. PCR amplification mixtures (25 µl) contained 12.5 µl of 2× Platinum Quantitative PCR SuperMix-UDG (Invitrogen Corp.), 0.625 µl of reverse primer (20 µM), 0.625 µl forward primers (20 µM), 0.625 µl Probe (10 µM) (ProbeLibrary Exiqon A/S, Denmark) and 5 µl diluted cDNA template. Real-time quantitative PCR was carried out using MX3000P PCR machine (Stratagene, USA) with the following cycling parameters: polymerase activation for 10 minutes at 95° C. and amplification for 40 cycles of 30 seconds at 95° C. and 60 seconds at 60° C. After amplification amplicons were validated during gele electrophoreses (E-Gel, Invitrogen Corp.).

Relative gene expression of iNOS and F4/80 were determined by quantitative RT-PCR comparative Ct method (Applied Biosystems. User Bulletin #2. ABI PRISM 7700 sequence detection system, 1997) using vehicle as calibrator. To normalize expression data 36B4 were used as internal standard. For each gene intron-spanning primers were designed using the public domain primer design software from ProbeLibrary Exiqon A/S (http://www.probelibrary.com/). Primer and probe number were as follows: 36B4 accession nr. X15096.1 sense (5'gtgtttgacaatggcagcat 3'), antisense (5'acagacgctggccacatt 3') and probe Rat#16. iNOS acc. nr. NM012611.2 sense (5' accatggagcatcccaagta 3'), antisense (5'cagcgcataccacttcagc 3') and probe Rat#71. F4/80 acc. nr. XM236797.2 sense (5'ggacttctccaagcctatcgt 3'), antisense (5'cctctcagacttctgctttgg 3') and probe Rat#26.

Figure 4A:
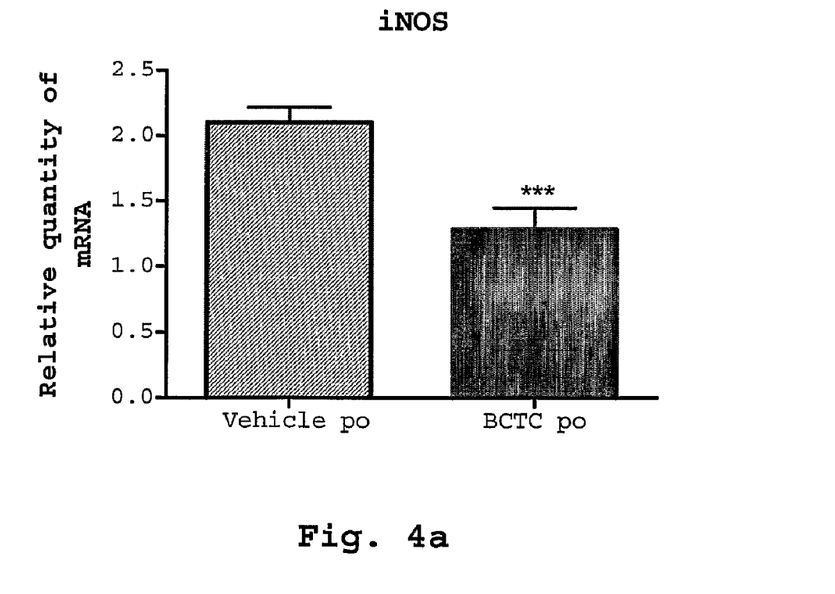
FIG. 4a and FIG. 4b show the relative levels of the inflammatory markers iNOS and F4/80, respectively, in the mesenteric adipose tissue in 9 month old Zucker obese rats 1 hour after they were given the capsaicin receptor antagonist BCTC (15 mg/kg) p.o. by gavage.
Figure 4B:
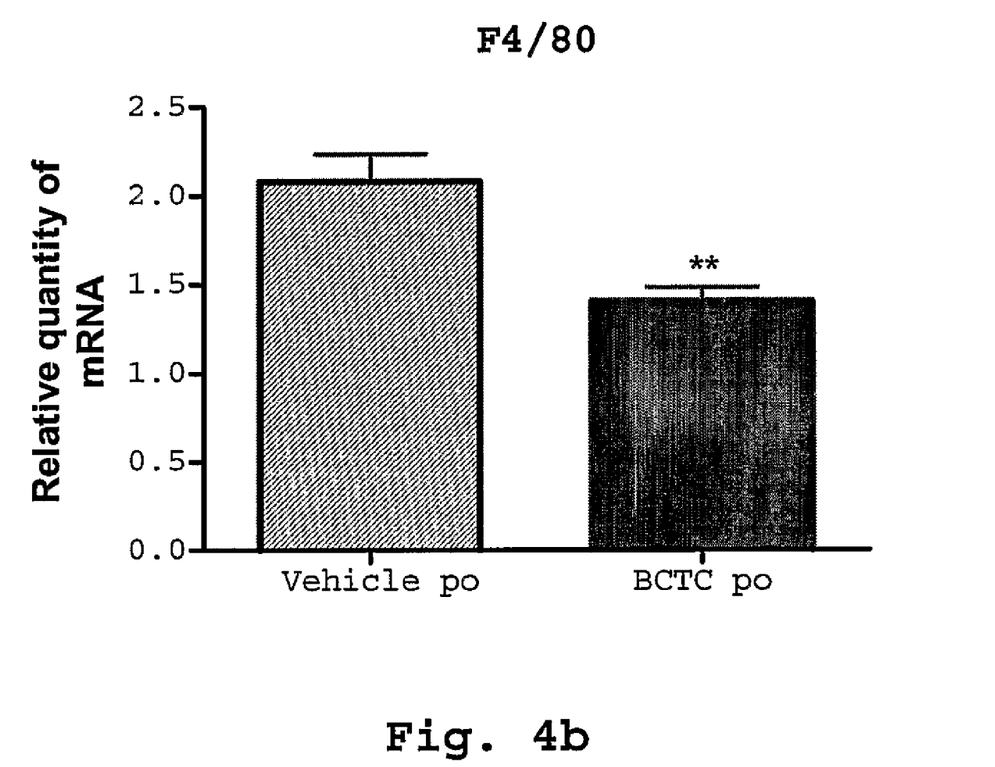

FIG. 4 shows the effect of BCTC on gene expression of iNOS and F4/80 in mesenteric adipose tissue of 9 month old Zucker obese rats. The BCTC treated rats (filled bar) display a significantly lower level of both iNOS (a) and F4/80 (b) 1 hour after BCTC (15 mg/kg) po. This suggests that BCTC mediates improvement of oral glucose tolerance as well as improvement of stimulated insulin release by reducing low-grade inflammation in tissue and that this is mediated by antagonising the capsaicin receptor.

This suggests that inactivating or down regulating the activity of the capsaicin receptor could be useful as novel pharmacological approach for the treatment of conditions where low-grade inflammation is associated with obesity and obesity-related disorders.

FIG. 1 and FIG. 2 indicate mice lacking the capsaicin receptor (VR1) do not develop impaired glucose tolerance after weeks on a high fat diet and that this is partially explained by a retained early insulin response to glucose.

FIG. 3 shows that oral glucose tolerance can be improved by oral administration of a capsaicin receptor antagonist (BCTC) in otherwise glucose intolerant male obese Zucker rats and that this is associated with an improvement of insulin secretion in response to oral glucose. FIG. 4 shows that local inflammation is reduced in the obese Zucker rat after BCTC, suggesting that the improvement of impaired glucose tolerance is associated with reduction of low-grade inflammation.

Inhibiting the activity of the capsaicin receptor in obesity or in obesity-related diseases and disorders thus appears promising as a new pharmacological approach.

BIBLIOGRAPHY

1. International Diabetes Federation (IDF). Diabetes Atlas 2000. (2000).
2. Gray, A. et al. Cost effectiveness of an intensive blood glucose control policy in patients with type 2 diabetes: economic analysis alongside randomised controlled trial (UKPDS 41). United Kingdom Prospective Diabetes Study Group. BMJ 320, 1373-1378 (2000).
3. UK Prospective Diabetes Study Group. UKPDS 40. Cost effectiveness analysis of improved blood pressure control in hypertensive patients with type 2 diabetes. *BMJ* 317, 720-726 (1998).
4. Mann, J. Stemming the tide of diabetes mellitus. *Lancet* 356, 1454-1455 (2000).
5. Knowler, W. C. et al. Reduction in the incidence of type 2 diabetes with lifestyle intervention or metformin. *NEW ENGL. J. MED.* 346, 393-403 (2002).
6. Fagerberg, B., Bokemark, L. & Hulthe, J. The metabolic syndrome, smoking, and antibodies to oxidized LDL in 58-year-old clinically healthy men. *Nutr. Metab. Carbiovasc. Dis.* 11, 227-235 (2001).
7. Liu, S. et al. Relation between a diet with a high glycemic load and plasma concentrations of high-sensitivity C-reactive protein in middle-aged women[1-3]. *Am J Clin N* 75, 492-498 (2002).
8. Temelkova-Kurktschiev, T. Subclinical inflammation in newly detected type II diabetes and impaired glucose tolerance [3]. *Diabetolog* 45, 151-2002.
9. Festa, A. et al. Chronic subclinical inflammation as part of the insulin resistance syndrome—The Insulin Resistance Atherosclerosis Study (IRAS). *Circulation* 102, 42-47 (2000).
10. Bhally, H. S. & Litvin, Y. Association between HbA1C and serum C-reactive protein levels in diabetes mellitus. *Diabetes* 50, A90 (2001).
11. Weyer, C. et al. Humoral markers of inflammation and endothelial dysfunction in relation to adiposity and in vivo insulin action in Pima Indians. *Atherosclerosis* 161, 233-242 (2002).
12. Julius, D. & Basbaum, A. I. Molecular mechanisms of nociception. *Nature* 413, 203-210 (2001).
13. Szolcsanyi, J., Jancso-Gabor, A. & Joo, F. Functional and fine structural characteristics of the sensory neuron blocking effect of capsaicin. *Naunyn Schmiedebergs Arch Pharmacol* 287, 157-169 (1975).
14. Barrachina, M. D., Martinez, V., Wei, J. Y. & Tache, Y. Leptin and CCK interact to reduce food intake in lean mice: Role of capsaicin-sensitive afferent neurons. *Methods and Findings in Experimental and Clinical Pharmacology* 19, 85 (1997).
15. Jancso-Gabor, A., Szolcsanyi, J. & Jancso, N. Irreversible Impairment of Thermo Regulation Induced by Capsaicin and Similar Pungent Substances in Rats and Guinea-Pigs. *J PHYSIOL (LONDON)* 206, 495-507 (1970).

16. Blumberg, P. M., Szallasi, A. & Acs, G. Resiniferatoxin: An ultrapotent capsaicin analogue. *Br J Pharmacol* 110, 45-62 (1993).
17. Szallasi, A. & Blumberg, P. M. Resiniferatoxin, a phorbol-related diterpene, acts as an ultrapotent analog of capsaicin, the irritant constituent in red pepper. *Neuroscienc* 30, 515-520 (1989).
18. Davey, P. T., Banner, S. E., Hamilton, T. C. & Sanger, G. J. Inhibition by capsazepine and ruthenium red of the pro- and anti-nociceptive effects of olvanil. *Br J Pharmacol* 115, 100P-1995.
19. Wittka, R., Wieland, H., Meyes, H. & Denzer, D. Comparison of two vanilloid receptor agonists: capsaicin and olvanil. *Life Sci* 26, Abstract-391 (2000).
20. Ralevic, V., Kendall, D. A., Jerman, J. C., Middlemiss, D. N. & Smart, D. Cannabinoid activation of recombinant and endogenous vanilloid receptors. *Eur J Pharmacol* 424, 211-219 (2001).
21. Ahern, G. P. & Premkumar, L. S. PKC induces vanilloid receptor channel activity. *Biophysical Journal* 80, 208a (2001).
22. Pomonis, J. D. et al. N-(4-Tertiarybutylphenyl)-4-(3-cholorphyridin-2-yl)tetrahydropyrazine-1 (2H)-carboxamide (BCTC), a novel, orally effective vanilloid receptor 1 antagonist with analgesic properties: II. in vivo characterization in rat models of inflammatory and neuropathic pain. *J Pharmacol Exp Ther* 306, 387-393 (2003).
23. Valenzano, K. J. et al. N-(4-tertiarybutylphenyl)-4-(3-chloropyridin-2-yl)tetrahydropyrazine-1 (2H)-carboxamide (BCTC), a novel, orally effective vanilloid receptor 1 antagonist with analgesic properties: I. in vitro characterization and pharmacokinetic properties. *J Phammacol Exp Ther* 306, 377-386 (2003).
24. Karlsson, S., Scheurink, A., Steffens, A. & Ahrén, B. Increased insulin secretion and glucose tolerance after neonatal capsaicin in mice. *Diabetolog* 37, A43 (1994).
25. Koopmans, S. J., Leighton, B. & DeFronzo, R. A. Neonatal de-afferentation of capsaicin-sensitive sensory nerves increases in vivo insulin sensitivity in conscious adult rats. *Diabetolog* 41, 813-820 (1998).
26. Gram, D. X. et al. Basal glycaemia and Glucose Tolerance is Improved after Resiniferatoxin in male Zucker Diabetic Fatty rats. Diabetologia 44 (Supplement 1), A 178. 2001. Ref Type: Abstract
27. Gram, D. X. et al. Capsaicin Desensitisation Delays the Progression of Type 2 Diabetes in the Zucker Fatty Rat. Diabetes 49 (Supplement 1), A428. 2000. Ref Type: Abstract
28. Gram, D. X., Brand, C. L., Wilken, M., Riebel, U. & Carr, R. D. DPPIV activity Is Decreased and Glucose Tolerance Improved by Sensory Nerve Denervatiion in the ZDF rat. Diabetes 50 (Suppl. 2), A515, 2167-PO. 2001. Ref Type: Abstract
29. Gram, D. X. et al. Sensory nerve desensitisation in Zucker Diabetic Fatty rats preserves in vitro insulin secretion. Diabetologia 43 (Supplement 1), A130. 2000. Ref Type: Abstract
30. Moesgaard, S. et al. Sensory nerve inactivation by resiniferatoxin improves insulin sensitivity in male obese Zucker rats. *Diabetes* 52, A68-2003.
31. Caterina, M. J. et al. The capsaicin receptor: A heat-activated ion channel in the pain pathway. *NATURE (LOND)* 389, 816-824 (1997).
32. Caterina, M. J. & Julius, D. The vanilloid receptor: A molecular gateway to the pain pathway. *Annu. Rev. Neurosci.* 24, 487-517 (2001).
33. Mezey, E. et al. Distribution of mRNA for vanilloid receptor subtype 1 (VR1), and VR1-like immunoreactivity, in the central nervous system of the rat and human. *Proc Natl Acad Sci USA* 97, 3655-3660 (2000).
34. Cortright, D. N. & Szallasi, A. Biochemical pharmacology of the vanilloid receptor TRPV1—An update. *Eur J Biochem* 271, 1814-1819 (2004).
35. Smart, D. et al. The endogenous lipid anandamide is a full agonist at the human vanilloid receptor (hVR1). *Br J Pharmacol* 129, 227-230 (2000).
36. Caterina, M. J. et al. Impaired nociception and pain sensation in mice lacking the capsaicin receptor. *Science (Washington D.C.)* 288, 306-313 (2000).
37. Davis, J. B. et al. Vanilloid receptor-1 is essential for inflammatory thermal hyperalgesia. *Nature* 405, 183-187 (2000).
38. Ahrén, B. & Pacini, G. Insufficient islet compensation to insulin resistance vs. reduced glucose effectiveness in glucose-intolerant mice. *American journal of physiology. Endocrinology and metabolism* 283, E738-E744 (2002).
39. La Fleur, S. E., Kalsbeek, A., Wortel, J., Fekkes, M. L. & Buijs, R. M. A daily rhythm in glucose tolerance: A role for the suprachiasmatic nucleus. *Diabetes* 50, 1237-1243 (2001).
40. Wahl, P., Foged, C., Tullin, S. & Thomsen, C. Iodo-resiniferatoxin, a new potent vanilloid receptor antagonist. *Mol. Pharmacol.* 59, 9-15 (2001).
41. Seabrook, G. R. et al. Functional properties of the high-affinity TRPV1 (VR1) vanilloid receptor antagonist (4-hydroxy-5-iodo-3-methoxyphenylacetate ester) iodo-resiniferatoxin. *J Pharmacol Exp Ther* 303, 1052-1060 (2002).
42. (WO 02/08211). 2002. Ref Type: Patent
43. Lee, J. et al. N-(3-acyloxy-2-benzylpropyl)-N'-[4-(methylsulfonylamino)benzyl]thioure a analogues: novel potent and high affinity antagonists and partial antagonists of the vanilloid receptor. *J Med Chem* 46, 3116-3126 (2003).
44. Wang, Y. et al. High affinity antagonists of the vanilloid receptor. *Mol. Pharmacol.* 62, 947-956 (2002).
45. Tóth, A., Blumberg, P. M., Chen, Z. & Kozikowski, A. P. Design of a high-affinity competitive antagonist of the vanilloid receptor selective for the calcium entry-linked receptor population. *Mol. Pharmacol.* 65, 282-291 (2004).
46. Yoon, J. et al. Chain-branched acyclic phenethylthiocarbamates as vanilloid receptor antagonists. *Bioorganic & Medicinal Chemistry Letters* 13, 1549-1552 (2003).
47. (WO 03/022809). 2003. Ref Type: Patent
48. (WO 02/090326). 2004. Ref Type: Patent
49. (WO 02/072536). 2002. Ref Type: Patent
50. (WO 03/014064). 2003. Ref Type: Patent
51. (WO 02/76946). 2002. Ref Type: Patent
52. McDonnell, M. E., Zhang, S., Nasser, N., Dubin, A. E. & Dax, S. L. 7-Hydroxynaphthalen-1-yl-urea and -amide antagonists of human vanilloid receptor 1. *Bioorganic & Medicinal Chemistry Letters* 14, 531-534 (2004).
53. Sun, Q. et al. 4-(2-pyridyl)piperazine-1-carboxamides: potent vanilloid receptor 1 antagonists. *Bioorg Med Chem Lett* 13, 3611-3616 (2003).
54. Garcia-Martinez, C. et al. Attenuation of thermal nociception and hyperalgesia by VR1 blockers. *Proc Natl Acad Sci USA* 99, 2374-2379 (2002).

55. Gunthorpe, M. J. et al. Identification and characterisation of SB-366791, a potent and selective vanilloid receptor (VR1/TRPV1) antagonist. *Neuropharmacology* 46, 133-149 (/1).

56. Sathianathan, V. et al. Insulin induces cobalt uptake in a subpopulation of rat cultured primary sensory neurons. *Neurosci. Lett.* 18, 2477-2486 (2003).

The invention claimed is:

1. A method for treating obesity in a mammal comprising: administering to the mammal a therapeutically-effective amount of a compound that is a halogenated analog of resiniferatoxin; N-(3-acyloxy-2-benzylpropyl)-N-[4-(methylsulfonylamino)benzyl-thiourea; [N-(4-tert-butylbenzyl)-N'-[4-(methylsulfonylamino)benzyl]thiourea]; [N-(4-tertbutylbenzyl)-N'-[3-fluoro-4-(methylsulfonylamino)benzyl]thiourea; N-(4-chlorobenzyl)-N'-(4-hydroxy-3-iodo-5-methoxybenzyl)thiourea; 4-(3-Chloro-pyridin-2-yl)-piperazine-1-carboxylic acid (4-tert-butyl-phenyl)-amide, or (N-(3-methoxyphenyl)-4-chlorocinnamide.

2. The method according to claim 1 wherein the mammal is a human.

3. The method according to claim 1, wherein the compound is 4-(3-Chloro-pyridin-2-yl)-piperazine-1-carboxylic acid (4-tert-butyl-phenyl)-amide.

4. A kit for treating obesity in a mammal in need thereof by inactivating or down regulating the activity of the capsaicin receptor, comprising a compound that is a halogenated analog of resiniferatoxin; N-(3-acyloxy-2-benzylpropyl)-N-[4-(methylsulfonylamino)benzyl-thiourea; [N-(4-tert-butylbenzyl)-N'-[4-(methylsulfonylamino)benzyl]thiourea]; [N-(4-tertbutylbenzyl)-N'-[3-fluoro-4-(methylsulfonylamino)benzyl]thiourea; N-(4-chlorobenzyl)-N'-(4-hydroxy-3-iodo-5-methoxybenzyl)thiourea; N-(4-tertiarybutylphenyl)-4-(3-chloropyridin-2-yl)tetrahydropyrazine-1(2H)-carboxamide, or (N-(3-methoxyphenyl)-4-chlorocinnamide.

5. A kit according to claim 4, wherein the mammal is a human.

* * * * *